United States Patent
Allen, IV et al.

(10) Patent No.: US 9,113,901 B2
(45) Date of Patent: Aug. 25, 2015

(54) MODULAR SURGICAL INSTRUMENT WITH CONTAINED ELECTRICAL OR MECHANICAL SYSTEMS

(75) Inventors: James D. Allen, IV, Broomfield, CO (US); Ryan C. Artale, Boulder, CO (US); Glenn A. Horner, Boulder, CO (US); Duane E. Kerr, Loveland, CO (US); Peter M. Mueller, Frederick, CO (US); Arlen J. Reschke, Longmont, CO (US); Robert M. Sharp, Boulder, CO (US); Robert B. Stoddard, Steamboat Springs, CO (US)

(73) Assignee: Covidien LP, Mansfield, MA (US)

( * ) Notice: Subject to any disclaimer, the term of this patent is extended or adjusted under 35 U.S.C. 154(b) by 506 days.

(21) Appl. No.: 13/470,775

(22) Filed: May 14, 2012

(65) Prior Publication Data

US 2013/0304059 A1    Nov. 14, 2013

(51) Int. Cl.
*A61B 18/14* (2006.01)
*A61B 17/285* (2006.01)
*A61B 17/29* (2006.01)
*A61B 18/00* (2006.01)

(52) U.S. Cl.
CPC .......... *A61B 18/1445* (2013.01); *A61B 17/285* (2013.01); *A61B 17/2909* (2013.01); *A61B 2018/0063* (2013.01); *A61B 2018/0091* (2013.01); *A61B 2018/00196* (2013.01); *A61B 2018/00589* (2013.01); *A61B 2018/00595* (2013.01); *A61B 2018/00601* (2013.01); *A61B 2018/00607* (2013.01); *A61B 2018/00982* (2013.01); *A61B 2018/1455* (2013.01)

(58) Field of Classification Search
None
See application file for complete search history.

(56) References Cited

U.S. PATENT DOCUMENTS

| | | | | |
|---|---|---|---|---|
| 2,113,246 | A | * | 4/1938 | Wappler ......................... 606/205 |
| 4,084,594 | A | * | 4/1978 | Mosior .......................... 606/170 |
| D249,549 | S | | 9/1978 | Pike |
| D263,020 | S | | 2/1982 | Rau, III |
| D295,893 | S | | 5/1988 | Sharkany et al. |
| D295,894 | S | | 5/1988 | Sharkany et al. |
| D298,353 | S | | 11/1988 | Manno |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 13/571,055 filed Aug. 9, 2012, Paul Guerra.

(Continued)

*Primary Examiner* — Kennedy Schaetzle

(57) ABSTRACT

A surgical instrument includes an elongated shaft module and a handle module selectively separable from one another. The elongated shaft module includes an elongated shaft member and a pair of jaw members supported at a distal end of the elongated shaft member, at least one of the jaw members moveable relative to the other jaw member between open and closed positions. The handle module includes a housing including an opening extending longitudinally therethrough. The opening is dimensioned to permit passage of the pair of jaw members in the closed position. The handle module also includes a movable handle movable relative to the housing to move the pair of jaw members between open and closed positions, and a lock to secure the elongated shaft module in place within the housing.

6 Claims, 6 Drawing Sheets

(56) References Cited

U.S. PATENT DOCUMENTS

| | | | |
|---|---|---|---|
| D299,413 S | 1/1989 | DeCarolis | |
| 5,035,248 A * | 7/1991 | Zinnecker | 600/564 |
| D343,453 S | 1/1994 | Noda | |
| 5,308,358 A * | 5/1994 | Bond et al. | 606/205 |
| 5,318,040 A * | 6/1994 | Kensey et al. | 600/567 |
| D348,930 S | 7/1994 | Olson | |
| D349,341 S | 8/1994 | Lichtman et al. | |
| 5,336,238 A | 8/1994 | Holmes | |
| 5,352,235 A | 10/1994 | Koros et al. | |
| D354,564 S | 1/1995 | Medema | |
| D358,887 S | 5/1995 | Feinberg | |
| 5,486,185 A * | 1/1996 | Freitas et al. | 606/142 |
| 5,489,290 A | 2/1996 | Furnish | |
| 5,507,774 A * | 4/1996 | Holmes et al. | 606/208 |
| 5,562,655 A | 10/1996 | Mittelstadt | |
| 5,571,100 A * | 11/1996 | Goble et al. | 606/41 |
| 5,578,052 A | 11/1996 | Koros et al. | |
| 5,603,723 A * | 2/1997 | Aranyi et al. | 606/205 |
| D384,413 S | 9/1997 | Zlock et al. | |
| 5,718,714 A | 2/1998 | Livneh | |
| H1745 H | 4/1998 | Paraschac | |
| 5,782,748 A | 7/1998 | Palmer et al. | |
| 5,810,876 A * | 9/1998 | Kelleher | 606/205 |
| D402,028 S | 12/1998 | Grimm et al. | |
| D408,018 S | 4/1999 | McNaughton | |
| 5,913,857 A * | 6/1999 | Ritchart et al. | 606/45 |
| 5,928,255 A | 7/1999 | Meade et al. | |
| D416,089 S | 11/1999 | Barton et al. | |
| 5,984,939 A * | 11/1999 | Yoon | 606/170 |
| D424,694 S | 5/2000 | Tetzlaff et al. | |
| D425,201 S | 5/2000 | Tetzlaff et al. | |
| 6,077,290 A * | 6/2000 | Marini | 606/205 |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| 6,428,538 B1 | 8/2002 | Blewett et al. | |
| D465,281 S | 11/2002 | Lang | |
| D466,209 S | 11/2002 | Bon | |
| 6,605,077 B2 | 8/2003 | Whittier et al. | |
| 6,666,875 B1 | 12/2003 | Sakurai et al. | |
| 6,740,079 B1 | 5/2004 | Eggers et al. | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 7,025,775 B2 * | 4/2006 | Gadberry et al. | 606/205 |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| 8,361,072 B2 * | 1/2013 | Dumbauld et al. | 606/51 |
| 2003/0195539 A1 | 10/2003 | Attinger et al. | |
| 2004/0254573 A1 | 12/2004 | Dycus et al. | |
| 2005/0080410 A1 | 4/2005 | Rioux et al. | |
| 2006/0129186 A1 * | 6/2006 | Gadberry et al. | 606/205 |
| 2008/0039892 A1 * | 2/2008 | Mitsuishi et al. | 606/208 |
| 2008/0319442 A1 | 12/2008 | Unger et al. | |
| 2009/0062788 A1 | 3/2009 | Long et al. | |
| 2009/0138006 A1 | 5/2009 | Bales et al. | |
| 2010/0312242 A1 * | 12/2010 | Odom | 606/52 |
| 2011/0112517 A1 | 5/2011 | Peine et al. | |
| 2011/0196402 A1 | 8/2011 | Robertson et al. | |
| 2012/0116394 A1 | 5/2012 | Timm et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 2 090 245 A1 | 8/2009 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |

(56) References Cited

FOREIGN PATENT DOCUMENTS

| | | |
|---|---|---|
| JP | 2001-3400 | 11/2001 |
| JP | 2002-528166 | 3/2002 |
| JP | 2002-136525 | 5/2002 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/045589 | 6/2002 |
| WO | WO 2005/110264 | 11/2005 |
| WO | 2006/134483 A2 | 12/2006 |

OTHER PUBLICATIONS

U.S. Appl. No. 13/571,821 filed Aug. 10, 2012, Joseph D. Bucciaglia.
U.S. Appl. No. 13/584,194 filed Aug. 13, 2012, Sean T. Dycus.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, Vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan., 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct., 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan., 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.

(56) References Cited

OTHER PUBLICATIONS

McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Intl Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Intl Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029;5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report Ep 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 168419.7 dated Oct. 20, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report Ep 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.

(56) References Cited

OTHER PUBLICATIONS

Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/USO4/03436 dated Mar. 3, 2005.
Int'l Search Report PCT/USO4/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
U.S. Appl. No. 08/926,869 filed Sep. 10, 1997, James G. Chandler.
U.S. Appl. No. 09/177,950 filed Oct. 23, 1998, Randel A. Frazier.
U.S. Appl. No. 09/387,883 filed Sep. 1, 1999, Dale F. Schmaltz.
U.S. Appl. No. 09/591,328 filed Jun. 9, 2000, Thomas P. Ryan.
U.S. Appl. No. 12/336,970 filed Dec. 17, 2008, Paul R. Sremcich.
U.S. Appl. No. 13/050,182 filed Mar. 17, 2011, Glenn A. Homer.
U.S. Appl. No. 13/072,945 filed Mar. 28, 2011, Patrick L. Dumbauld.
U.S. Appl. No. 13/080,383 filed Apr. 5, 2011, David M. Garrison.
U.S. Appl. No. 13/085,144 filed Apr. 12, 2011, Keir Hart.
U.S. Appl. No. 13/091,331 filed Apr. 21, 2011, Jeffrey R. Townsend.
U.S. Appl. No. 13/102,573 filed May 6, 2011, John R. Twomey.
U.S. Appl. No. 13/102,604 filed May 6, 2011, Paul E. Ourada.
U.S. Appl. No. 13/108,093 filed May 16, 2011, Boris Chernov.
U.S. Appl. No. 13/108,129 filed May 16, 2011, Boris Chernov.
U.S. Appl. No. 13/108,152 filed May 16, 2011, Boris Chernov.
U.S. Appl. No. 13/108,177 filed May 16, 2011, Boris Chernov.
U.S. Appl. No. 13/108,196 filed May 16, 2011, Boris Chernov.
U.S. Appl. No. 13/108,441 filed May 16, 2011, Boris Chernov.
U.S. Appl. No. 13/108,468 filed May 16, 2011, Boris Chernov.
U.S. Appl. No. 13/111,642 filed May 19, 2011, John R. Twomey.
U.S. Appl. No. 13/111,678 filed May 19, 2011, Nikolay Kharin.
U.S. Appl. No. 13/113,231 filed May 23, 2011, David M. Garrison.
U.S. Appl. No. 13/157,047 filed Jun. 9, 2011, John R. Twomey.
U.S. Appl. No. 13/162,814 filed Jun. 17, 2011, Barbara R. Tyrrell.
U.S. Appl. No. 13/166,477 filed Jun. 22, 2011, Daniel A. Joseph.
U.S. Appl. No. 13/166,497 filed Jun. 22, 2011, Daniel A. Joseph.
U.S. Appl. No. 13/179,919 filed Jul. 11, 2011, Russell D. Hempstead.
U.S. Appl. No. 13/179,960 filed Jul. 11, 2011, Boris Chernov.
U.S. Appl. No. 13/179,975 filed Jul. 11, 2011, Grant T. Sims.
U.S. Appl. No. 13/180,018 filed Jul. 11, 2011, Chase Collings.
U.S. Appl. No. 13/183,856 filed Jul. 15, 2011, John R. Twomey.
U.S. Appl. No. 13/185,593 filed Jul. 19, 2011, James D. Allen, IV.
U.S. Appl. No. 13/204,841 filed Aug. 8, 2011, Edward J. Chojin.
U.S. Appl. No. 13/205,999 filed Aug. 9, 2011, Jeffrey R. Unger.
U.S. Appl. No. 13/212,297 filed Aug. 18, 2011, Allan J. Evans.
U.S. Appl. No. 13/212,308 filed Aug. 18, 2011, Allan J. Evans.
U.S. Appl. No. 13/212,329 filed Aug. 18, 2011, Allan J. Evans.
U.S. Appl. No. 13/212,343 filed Aug. 18, 2011, Duane E. Kerr.
U.S. Appl. No. 13/223,521 filed Sep. 1, 2011, John R. Twomey.
U.S. Appl. No. 13/227,220 filed Sep. 7, 2011, James D. Allen, IV.
U.S. Appl. No. 13/228,742 filed Sep. 9, 2011, Duane E. Kerr.
U.S. Appl. No. 13/231,643 filed Sep. 13, 2011, Keir Hart.
U.S. Appl. No. 13/234,357 filed Sep. 16, 2011, James D. Allen, IV.
U.S. Appl. No. 13/236,168 filed Sep. 19, 2011, James D. Allen, IV.
U.S. Appl. No. 13/236,271 filed Sep. 19, 2011, Monte S. Fry.
U.S. Appl. No. 13/243,628 filed Sep. 23, 2011, William Ross Whitney.
U.S. Appl. No. 13/247,778 filed Sep. 28, 2011, John R. Twomey.
U.S. Appl. No. 13/247,795 filed Sep. 28, 2011, John R. Twomey.
U.S. Appl. No. 13/248,976 filed Sep. 29, 2011, James D. Allen, IV.
U.S. Appl. No. 13/249,013 filed Sep. 29, 2011, Jeffrey R. Unger.
U.S. Appl. No. 13/249,024 filed Sep. 29, 2011, John R. Twomey.
U.S. Appl. No. 13/251,380 filed Oct. 3, 2011, Duane E. Kerr.
U.S. Appl. No. 13/277,373 filed Oct. 20, 2011, Glenn A. Homer.
U.S. Appl. No. 13/277,926 filed Oct. 20, 2011, David M. Garrison.
U.S. Appl. No. 13/277,962 filed Oct. 20, 2011, David M. Garrison.
U.S. Appl. No. 13/293,754 filed Nov. 10, 2011, Jeffrey M. Roy.
U.S. Appl. No. 13/306,523 filed Nov. 29, 2011, David M. Garrison.
U.S. Appl. No. 13/306,553 filed Nov. 29, 2011, Duane E. Kerr.
U.S. Appl. No. 13/308,104 filed Nov. 30, 2011, John R. Twomey.
U.S. Appl. No. 13/312,172 filed Dec. 6, 2011, Robert J. Behnke, II.
U.S. Appl. No. 13/324,863 filed Dec. 13, 2011, William H. Nau, Jr.
U.S. Appl. No. 13/344,729 filed Jan. 6, 2012, James D. Allen, IV.
U.S. Appl. No. 13/355,829 filed Jan. 23, 2012, John R.Twomey.
U.S. Appl. No. 13/357,979 filed Jan. 25, 2012, David M. Garrison.
U.S. Appl. No. 13/358,136 filed Jan. 25, 2012, James D. Allen, IV.
U.S. Appl. No. 13/360,925 filed Jan. 30, 2012, James H. Orszulak.
U.S. Appl. No. 13/400,290 filed Feb. 20, 2012, Eric R. Larson.
U.S. Appl. No. 13/404,435 filed Feb. 24, 2012, Kim V. Brandt.
U.S. Appl. No. 13/404,476 filed Feb. 24, 2012, Kim V. Brandt.
U.S. Appl. No. 13/412,879 filed Mar. 6, 2012, David M. Garrison.
U.S. Appl. No. 13/412,897 filed Mar. 6, 2012, Joanna Ackley.
U.S. Appl. No. 13/421,373 filed Mar. 15, 2012, John R. Twomey.
U.S. Appl. No. 13/430,325 filed Mar. 26, 2012, William H. Nau, Jr.
U.S. Appl. No. 13/433,924 filed Mar. 29, 2012, Keir Hart.
U.S. Appl. No. 13/448,577 filed Apr. 17, 2012, David M. Garrison.
U.S. Appl. No. 13/460,455 filed Apr. 30, 2012, Luke Waaler.
U.S. Appl. No. 13/461,335 filed May 1, 2012, James D. Allen, IV.
U.S. Appl. No. 13/461,378 filed May 1, 2012, James D. Allen, IV.
U.S. Appl. No. 13/461,397 filed May 1, 2012, James R. Unger.
U.S. Appl. No. 13/461,410 filed May 1, 2012, James R. Twomey.
U.S. Appl. No. 13/464,569 filed May 4, 2012, Duane E. Kerr.
U.S. Appl. No. 13/466,274 filed May 8, 2012, Stephen M. Kendrick.
U.S. Appl. No. 13/467,767 filed May 9, 2012, Duane E. Kerr.
U.S. Appl. No. 13/470,543 filed May 14, 2012, Sean T. Dycus.
U.S. Appl. No. 13/470,775 filed May 14, 2012, James D. Allen, IV.
U.S. Appl. No. 13/470,797 filed May 14, 2012, John J. Kappus.
U.S. Appl. No. 13/482,589 filed May 29, 2012, Eric R. Larson.
U.S. Appl. No. 13/483,733 filed May 30, 2012, Dennis W. Butcher.
U.S. Appl. No. 13/488,093 filed Jun. 4, 2012, Kristin D. Johnson.
U.S. Appl. No. 13/491,853 filed Jun. 8, 2012, Jessica E. Olson.
U.S. Appl. No. 13/537,517 filed Jun. 29, 2012, David N. Heard.
U.S. Appl. No. 13/537,577 filed Jun. 29, 2012, Tony Moua.
U.S. Appl. No. 13/550,322 filed Jul. 16, 2012, John J. Kappus.
Partial European Search Report from Application No. EP 13167430.1 dated Sep. 4, 2013.
Australian Examination Report dated Apr. 7, 2015 from Application No. AU 2013205068.
Extended European Search Report from Application No. EP 13167430.1 dated Nov. 22, 2013.
International Search Report from EP Application No. 12168303.1 mailed Nov. 5, 2012.

* cited by examiner

MODULAR SURGICAL INSTRUMENT WITH CONTAINED ELECTRICAL OR MECHANICAL SYSTEMS

BACKGROUND

1. Technical Field

The present disclosure relates generally to the field of reposable or reusable surgical instruments. In particular, the disclosure relates to instruments having contained operating systems therein, which facilitates refurbishment of the instruments.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis. Thereafter, the sealed tissue may be transected by advancing a knife through the jaws. A detailed discussion of the use of an electrosurgical forceps may be found in U.S. Pat. No. 7,255,697 to Dycus et al.

In use, various tissue-contacting components of an electrosurgical forceps tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use, even in a single surgical procedure. In order to provide clean electrodes and a sharp knife for a particular surgical procedure, a brand new instrument is often used. Once the procedure is complete, the used instrument is discarded.

Instruments that are reposable, or reusable for multiple procedures, reduce the instrumentation costs per procedure. Providing a reusable electrosurgical forceps, however, presents various challenges. For example, the complexity of an electrosurgical forceps tends to result in fairly labor intensive cleaning procedures to prepare the forceps for subsequent use. Improper cleaning may result in dangerous contamination being introduced surgical site. Also, some reusable forceps have removable and replaceable components to provide clean surfaces for each use. Many of these instruments require arduous disassembly and reassembly procedures that require extensive training, and may discourage use of the instrument.

SUMMARY

The present disclosure describes a surgical instrument for treating tissue. The instrument includes an elongated shaft module and a handle module. The elongated shaft module includes an elongated shaft member and a pair of jaw members supported at a distal end of the elongated shaft member. At least one of the jaw members is moveable relative to the other jaw member between open and closed positions. The handle module includes a housing having an opening extending longitudinally therethrough. The opening is dimensioned to permit passage of the pair of jaw members in the closed position. The handle assembly also includes a movable handle that is movable relative to the housing and operatively coupled to the pair of jaw members such that at least one of the jaw members is induced to move relative to the other jaw member between open and closed positions in response to movement of the movable handle with respect to the housing, and a lock movable between a first position wherein the lock engages the elongated shaft module to secure the elongated shaft module in place within the housing, and a second position wherein the lock is disengaged from the elongated shaft module to permit the elongated shaft module to be separated from the handle module.

The elongated shaft module may include a connector at a proximal end thereof for coupling the instrument to an external source of electrosurgical energy. The elongated shaft module may also include a contained electrical system therein, wherein the electrical system includes an electrical pathway extending between the connector and the end effector that is contained in a substantially moisture impervious casing.

The elongated shaft module may include a reciprocating drive rod extending at least partially through the elongated shaft member and operably coupled to the end effector and the movable handle to induce movement of the jaw members between the open and closed positions in response to movement of the movable handle with respect to the housing to reciprocate the drive rod. The elongated shaft module may include a sealing member coupled to the elongated shaft member at a distal end thereof, and the sealing member may be disposed between the elongated shaft member and the reciprocating drive rod to discourage contaminants from entering the elongated shaft member. The sealing member may be constructed of at least one of an o-ring, a wiper seal and a bellows.

The elongated shaft module may also include a flexible seal member disposed between the jaw members and the outer shaft member, and the flexible seal member may be constructed of heat-shrink tubing. The jaw members may be coupled to the reciprocating drive rod such that the jaw members are induced retract into elongated shaft member in response to reciprocation of the drive rod.

According to another aspect of the disclosure, a surgical instrument includes a handle module including at least one handle providing gripping surfaces for holding the instrument by hand, and a drive assembly selectively removable from the handle assembly. The drive assembly includes an elongated shaft member defining a longitudinal axis and an end effector supported at a distal end of the elongated shaft member. The end effector includes a pair of opposed jaw members wherein at least one of the jaw members is movable relative to the elongated shaft member between open and closed positions with respect to the other jaw member. The drive assembly also includes a reciprocating drive member extending at least partially though the elongated shaft member. The reciprocating drive member operably coupled to the end effector to induce movement of the jaw members between the open and closed positions in response to longitudinal reciprocation of the drive member. A motor is operable to move the reciprocating drive member longitudinally through the elongated shaft, and a substantially moisture-impervious housing substantially surrounds the motor and the reciprocating drive member. An actuator is supported on the housing, and is operable to activate the motor.

The motor may comprise a servomotor or a linear motor. The linear motor may include an electrical coil supported on the elongated shaft member and a magnet supported on the reciprocating drive member, wherein the magnet is longitudinally movable in response to a current in the electrical coil.

The drive assembly may include a cable extending from the housing that is connectable to a source of electrosurgical energy. The cable may be in electrical communication with an electrical conduit extending through the elongated shaft member to transmit an electrosurgical current to the end effector. The drive assembly may also include at least one of a post and a slot disposed thereon configured to snap-fit to at least one of a post and a slot disposed on the handle assembly.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
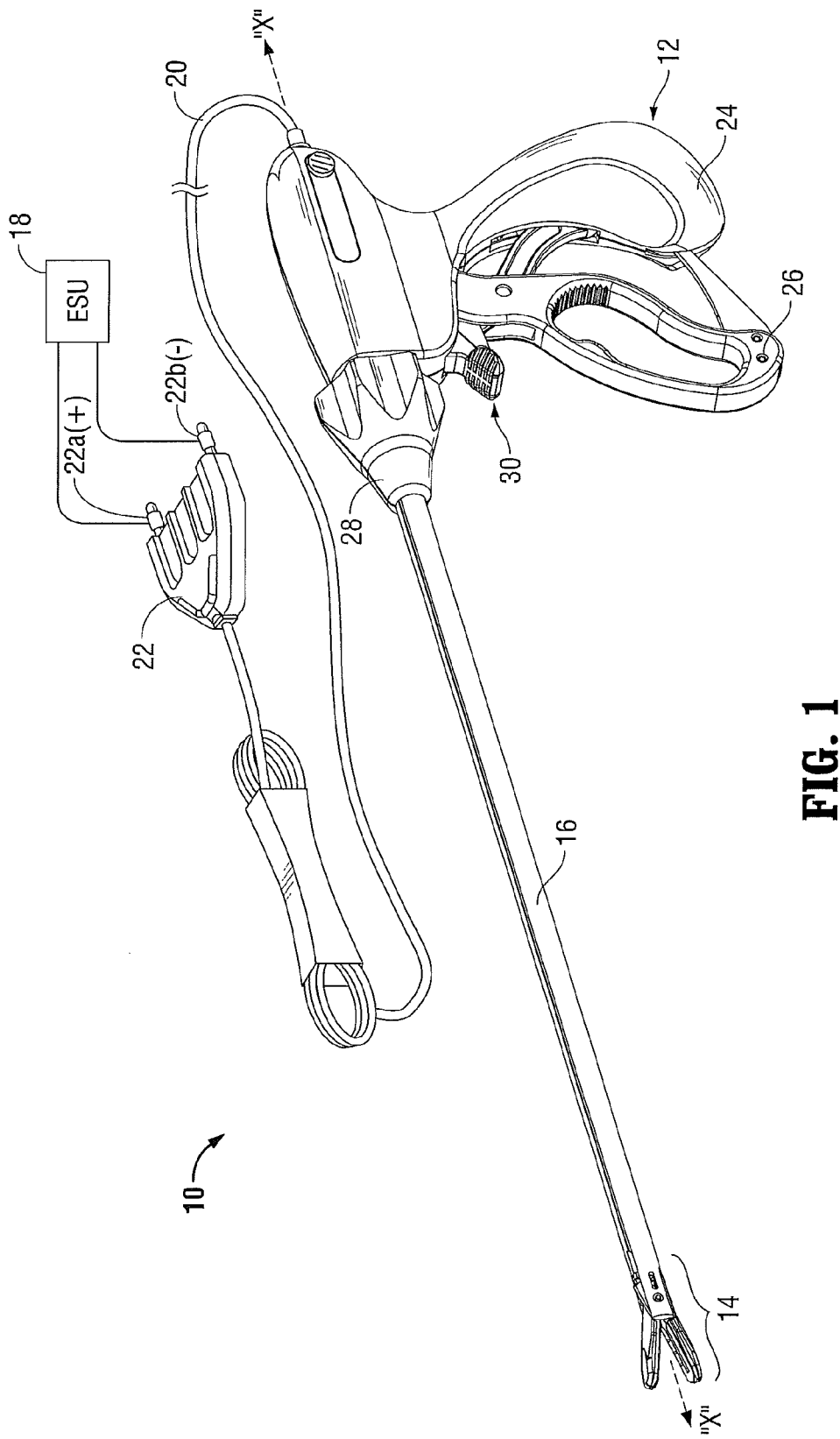
FIG. 1 is a perspective view of an endoscopic surgical instrument having a handle assembly and a removable shaft assembly in accordance with an embodiment of the present disclosure.

Referring initially to FIG. 1, an embodiment of an electrosurgical instrument 10 is depicted. The instrument 10 includes a handle assembly 12 for remotely controlling an end effector 14 through an elongated shaft member 16. Although this configuration is typically associated with instruments for use in laparoscopic or endoscopic surgical procedures, various aspects of the present disclosure may be practiced with traditional open instruments, and in connection with endoluminal procedures as well.

The instrument 10 is coupled to a source of electrosurgical energy, e.g., an electrosurgical generator 18. The generator 18 may include devices such as the LIGASURE® Vessel Sealing Generator and the Force Triad® Generator as sold by Covidien. A cable 20 extends between the handle assembly 12 and the generator 18, and includes a connector 22 for coupling the instrument 10 to the external generator 18. In other embodiments (not shown) a battery powered instrument may be provided in which a generator and connector may be internal or integral to the instrument. The connector 22 includes two prong members 22a and 22b that are dimensioned to physically and electrically connect the instrument 10 to opposite terminals, e.g., positive or active (+) and negative or return (−) terminals associated with the generator 18. Thus, bipolar energy may be provided through the instrument 10. Alternatively, the instrument 10 may be configured for delivering monopolar energy to the tissue. In a monopolar configuration, the instrument 10 delivers electrosurgical energy from an active terminal, e.g. (+), while a return pad (not shown) is placed generally beneath a patient and provides a return path to the opposite terminal, e.g. (−), of the generator 18.

To control the end effector 14, the handle assembly 12 includes a stationary handle 24 and movable handle 26. The movable handle 26 may be separated and approximated relative to the stationary handle 24 to respectively open and close the end effector 14. A rotation knob 28 is provided on the handle assembly 12 to permit rotation of the elongated shaft member 16 and the end effector 14 about a longitudinal axis X-X defined by the elongated shaft member 16. A trigger 30 is also disposed on the handle assembly 12, and is operable to extend and retract a knife 136 (see, e.g., FIG. 5A) through the end effector 14. A footswitch (not shown) may be provided to initiate and terminate the delivery of electrosurgical energy to the end effector 14.

Figure 2:
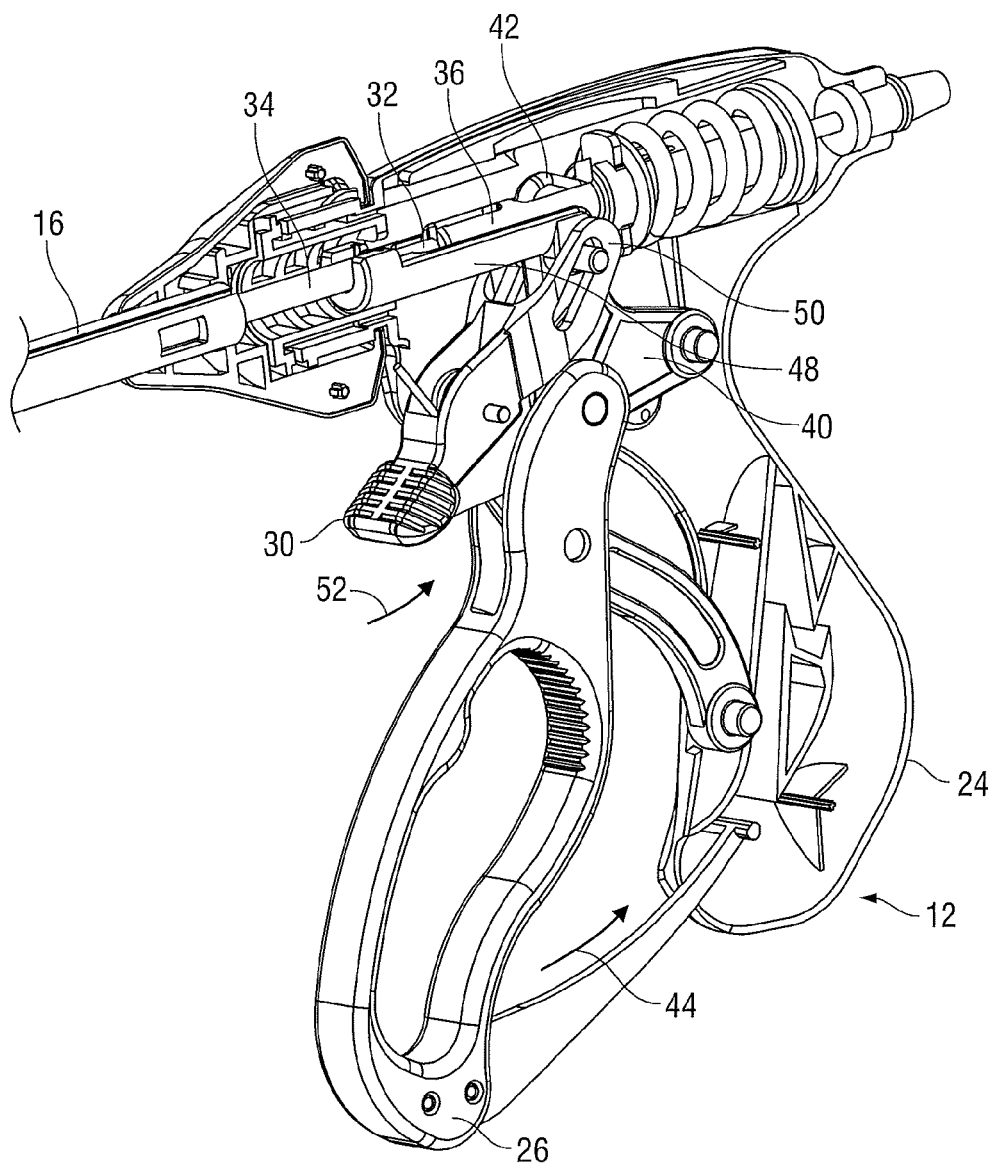
FIG. 2 is a perspective view of the handle assembly of the FIG. 1 with a portion of a housing removed depicting interior components of the instrument.

Referring now to FIG. 2, the handle assembly 12 is operatively coupled to the end effector 14 (FIG. 1) through a reciprocating drive rod 32 and a knife tube 34 that extend through the elongated shaft member 16. First, the drive rod 32 is operably coupled to the movable handle 26 by an inner sleeve 36 and a link 40 such that pivotal movement of the movable handle 26 induces longitudinal motion of the drive rod 32. The drive rod 32 and the inner sleeve 36 engage one another such that longitudinal motion is transferred therebetween. The inner sleeve 36 and the link 40 engage one another through an upper flange 42 of the link 40 such that pivotal movement of the link 40 induces longitudinal motion of the inner sleeve 36, and, conversely, such that longitudinal motion of the inner sleeve 36 induces pivotal motion of the link 40. The link 40 is pivotally coupled to the movable handle 26 such that pivotal motion may be transferred therebetween. In use, a surgeon may pivot the movable handle 26 toward the stationary handle 24 in the direction of arrow 44, which induces the link 40 to pivot such that the upper flange 42 of the link 40 moves proximally. The proximal movement of the upper flange 42, in turn, draws the inner sleeve 36 and the drive rod 32 in a proximal direction. The proximal movement of the drive rod 32 induces a pair of jaw members 140, 142 (FIG. 5A) of the end effector 14 to move from an open configuration (FIG. 5A) to a closed configuration (FIG. 3) as described in greater detail below with reference to FIG. 5A.

Next, the knife tube 34 is operably coupled to the trigger 30 by an outer sleeve 48. The knife tube 34 and the outer sleeve 48 engage one another such that longitudinal motion is transferred therebetween. The outer sleeve 48 and the trigger 30 engage one another through an upper flange 50 of the trigger 30 such that pivotal movement of the trigger 30 induces longitudinal motion of the outer sleeve 48. In use, a surgeon may pivot the trigger 30 toward the stationary handle 24 in the direction of arrow 52, which induces the upper flange 50 of the trigger 30 to move distally. The distal movement of the upper flange 50, in turn, drives the outer sleeve 48 and the knife tube 34 in a distal direction. The knife tube 34 is coupled to a knife 136 (FIG. 5A) such that the distal movement of the of the knife tube 34 advances the knife through the end effector 14 as described in greater detail below with reference to FIG. 5A.

Figure 3:
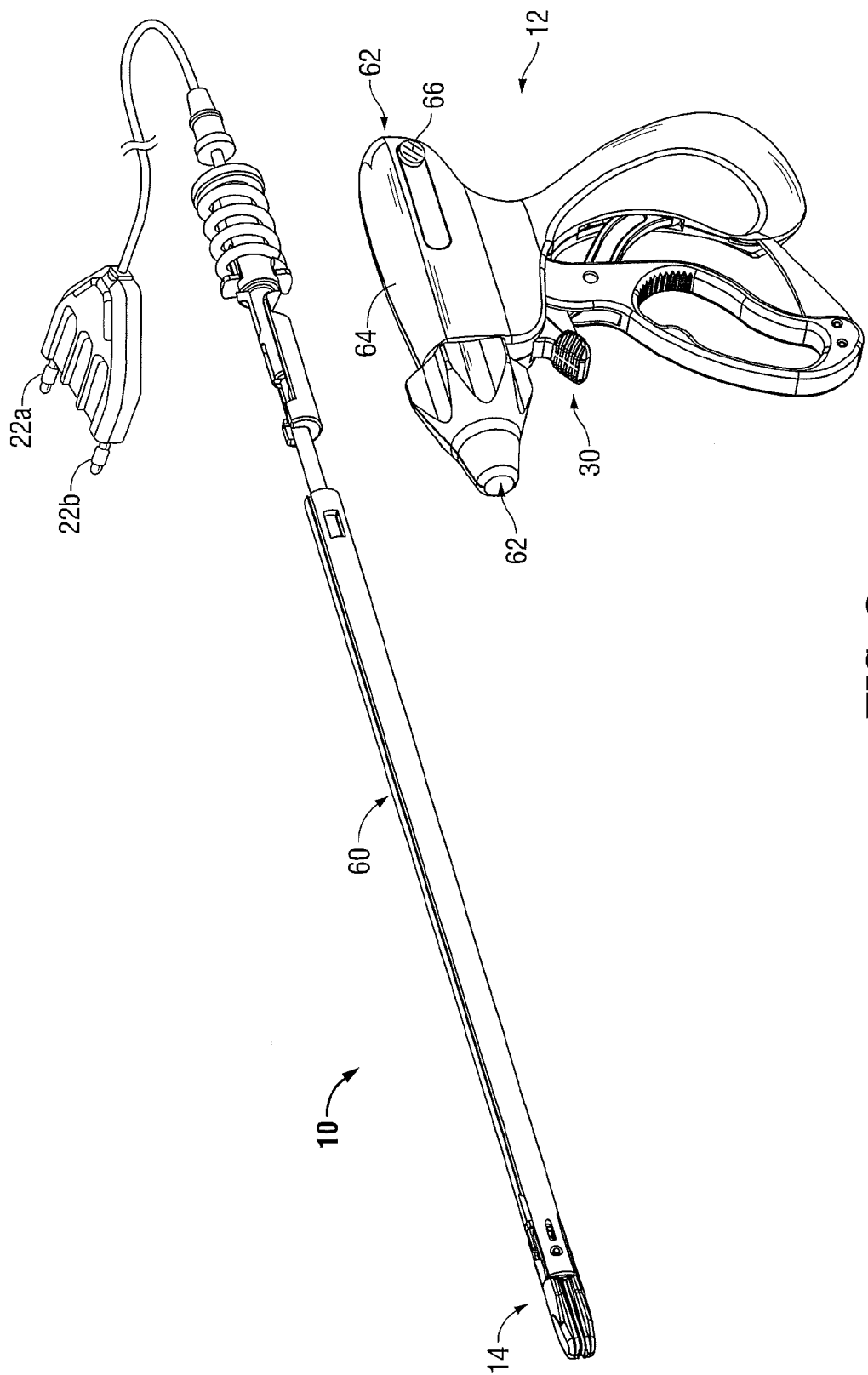
FIG. 3 is a perspective view of the instrument of FIG. 1 depicting the removable shaft assembly separated from the handle assembly.

Referring now to FIG. 3, the instrument 10 is selectively separable into two main modules including the handle assembly 12 and an elongated shaft assembly 60. Separation of the two modules 12, 60 permits use of the instrument in a modular fashion. For example, an alternate elongated shaft assembly (not shown) may be substituted for elongated shaft assembly 60 to provide a more appropriate length for a particular surgical operation. Additionally, separation of the two modules 12, 60 may facilitate cleaning and refurbishment of the instrument 10 by providing ready access to interior components of the instrument 10.

The elongated shaft assembly 60 includes a fully contained electrical system. The entire electrically conductive pathway through the instrument 10, from the prong members 22a, 22b to the end effector 14, is part of the elongated shaft assembly 60. Thus, no electrical connections need to be established when assembling the handle assembly 12 and the elongated shaft assembly 60 and the entire electrical pathway may be enclosed in a substantially moisture-impervious casing.

The handle assembly 12 includes a longitudinal opening 62 extending through a housing 64 thereof for receiving the elongated shaft assembly 60. The opening 62 is configured such that the end effector 14 may pass therethrough when arranged in the closed configuration. Thus, the elongated shaft assembly 60 may be assembled to the handle assembly by inserting the end effector 14 into the opening 62 on the proximal side of the instrument 10, and advancing the elongated shaft assembly 60 distally. The trigger 30 may be biased to engage the outer sleeve 48 (FIG. 2), and the link 40 (FIG. 2) may be biased to engage the inner sleeve 36 (FIG. 2) upon sufficient advancement of the elongated shaft assembly 60 distally through the opening 62. The handle assembly 12 also includes a lock 66 thereon, which would permit a surgeon to selectively provide a positive lock to maintain the engagement of the elongated shaft assembly 60 with the handle assembly 12. The lock 66 may be movable between a first position wherein the lock 66 engages the elongated shaft assembly 60 to lock the elongated shaft assembly in place, and a second position wherein the lock 66 disengages the elongated shaft assembly to permit the elongated shaft assembly 60 to be separated from the handle assembly 12.

This modular configuration may be convenient for an operator to assemble since the end effector 14 is provided in a fully assembled condition. Many of the relatively small or delicate components of the end effector 14, such as pivot pin 148 (FIG. 5A), drive pin 144 (FIG. 5A) and knife 136 (FIG. 5A), are preassembled to form a substantial modular unit that is convenient to manipulate by hand. This modular configuration also locates the electrically engaging components, e.g., prong members 22a, 22b, at a proximal location substantially spaced from a wet surgical site during use. Proximally locating the electrically engaging components may preserve functionality over time, and may facilitate cleaning of a modular system.

Figure 4:
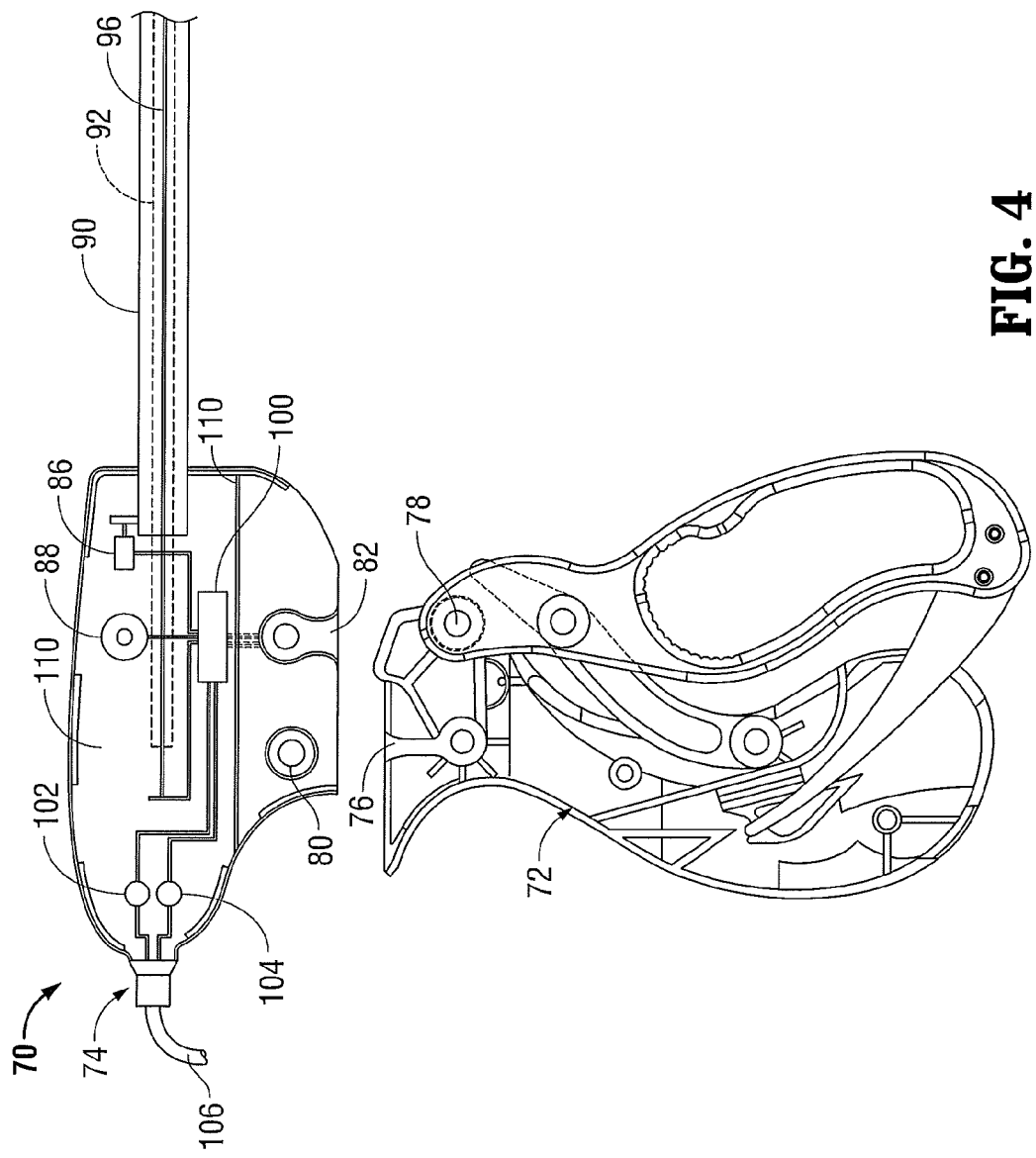
FIG. 4 is a partial, schematic view of an alternate embodiment of an instrument in accordance with the present disclosure including a handle assembly and a removable module having a contained actuation system.

Referring now to FIG. 4, an alternate embodiment of a surgical instrument 70 includes two main components including a handle assembly 72 and a drive assembly 74. The handle assembly 72 includes a slot 76 and a post 78 thereon, which permits the handle assembly 72 to snap onto a post 80 and slot 82 disposed on the drive assembly 74. The handle assembly 72 may provide gripping surfaces for surgeon to hold the instrument 70, but the handle assembly 72 may be otherwise inoperable to control the drive assembly 74.

The drive assembly 74 includes a fully contained electrical system as well as a fully contained mechanical system for controlling the instrument 70. The mechanical system of the drive assembly 74 includes a pair of servomotors 86 and 88 for generating physical or mechanical motion in the instrument 70. The motor 86 engages an elongated shaft member 90 and is operable to rotate the elongated shaft member 90 about a longitudinal axis. Motor 88 engages a drive rod 92, and is operable to translate the drive rod 92 longitudinally through the elongated shaft member 90. Thus, the servomotors 86 and 88 are operable to rotate, open and close and end effector (not shown) as described above with reference to FIG. 1. In other embodiments (not shown), an additional motor may be provided to translate a knife through the elongated shaft.

The electrical system of the drive assembly 74 includes an electrical conduit 96 extending through the elongated shaft member 90. The electrical conduit 96 transmits an electrosurgical current through the elongated shaft member 90 to provide an end effector with an electrosurgical cutting (e-cutting) capability. Electrosurgical cutting is described in greater detail in U.S. Pat. No. 7,270,664 to Johnson et al. The electrical system also includes a circuit board 100. The circuit board 100 is electrically coupled to the motors 88, 86 and to the electrical conduit 96 for providing instructions and electrical power thereto. The circuit board is also electrically coupled to a pair of buttons 102, 104, which a surgeon may depress to activate the motors 88, 86 and to the electrical conduit 96. The buttons 102, 104 are in electrical communication with a cable 106, which may connect the instrument 70 to a source of electrosurgical energy.

A housing 110 surrounds the electrical and mechanical systems of the drive assembly 74, and no electrical connections or mechanical connections to transmit physical motion need to be established to assemble the drive assembly 74 to the handle assembly 72. The housing 110 may thus be configured with a minimum of gaps or crevices where contaminants may become lodged during a surgical procedure. The housing 110 may be substantially impervious to moisture to encase the electrical and mechanical systems therein. This facilitates cleaning and sterilization of the instrument 70 before subsequent use.

Figure 5A:
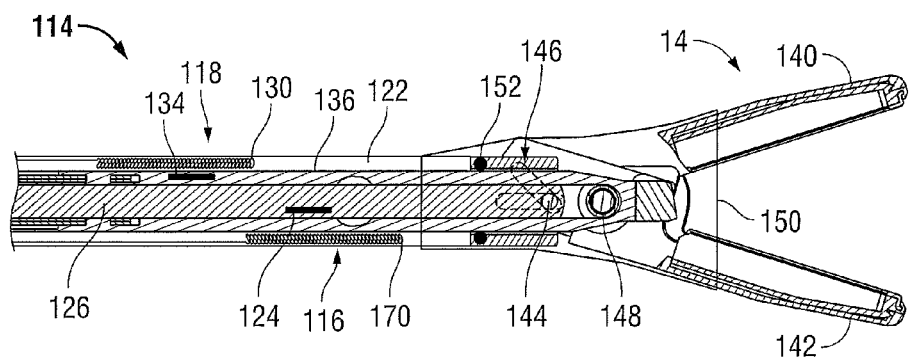
FIG. 5A is a partial, schematic view of an alternate embodiment of an instrument in accordance with the present disclosure including contained actuation system with a distal end seal.

Referring now to FIG. 5A, an alternate embodiment of a surgical instrument 114 includes a mechanical system having linear motors 116, 118 for generating physical motion in the instrument 114. The first linear motor 116 includes an electrical coil 120 embedded in an outer shaft member 122 of the instrument 114 and a magnet 124 embedded in a drive rod 126. The second linear motor 118 includes an electrical coil 130 embedded in the outer shaft member 122 and a magnet 134 embedded in a knife 136. By initiating an appropriate electrical current through the coils 120, 130, relative longitudinal motion between the outer shaft member 122 and drive rod 126 and the knife 136 may be induced.

By delivering an appropriate electric current to electrical coil 120, the magnet 124 may be induced to move longitudinally, and thus the drive rod 126 may be induced to move longitudinally since the magnet 124 is imbedded in the drive rod 126. Longitudinal motion of the drive rod 126 induces the end effector 14 to move between the open configuration depicted and the closed configuration (FIG. 3). The end effector 14 includes a pair of jaw members 140, 142, which are coupled to the drive rod 126 by a drive pin 144. The drive pin 144 extends through slots, e.g. drive slot 146, defined in the jaw members 140, 142. The drive slot 146 is arranged obliquely with respect to the elongated shaft member 122 such that longitudinal motion of the drive rod 126 and drive pin 144 induces the jaw members 140, 142 pivot about a pivot pin 148. Thus, activating the linear motor 116 induces the end effector 14 to move between the open and closed configurations.

By delivering an appropriate electric current to electrical coil 130, the magnet 134 may be induced to move longitudinally, and thus the knife 136 may be induced to move longitudinally since the magnet 134 is imbedded in the knife 136. Thus, activating the linear motor 118 may induce the knife 136 to move through the end effector 14 to transect tissue clamped between the jaw members 140, 142.

Since the linear motors 116 and 118 may be activated by electrical signals, the mechanical system of instrument 114 does not require inputs of physical movement from a surgeon to operate the end effector 14. Thus, a proximal end (not shown) of the instrument 114 may be readily sealed. The mechanical system may be fully contained by sealing a distal end of the instrument 114 at appropriate locations. The instrument 114 includes a flexible seal member 150 disposed between the jaw members 140, 142 and the outer shaft member 122. The flexible seal may be constructed of heat-shrink tubing or a similar material, and serves to discourage contaminants from entering the outer shaft member 122. An additional seal member 152 is disposed between the outer shaft member 122 and the knife 136. The seal member 152 is constructed as an o-ring, and prevents contaminants from traveling proximally through the outer shaft member 122. The seals 150, 152 are substantially impervious to moisture, and accommodate the motion of the jaw members 140, 142 and the knife 146 with respect to the outer shaft member 122. The seals facilitate cleaning or sterilization of the instrument 114 since the cleaning or a sterilization medium does not need to penetrate deep into the shaft member 122 or access intricately moving components.

Figure 5B:
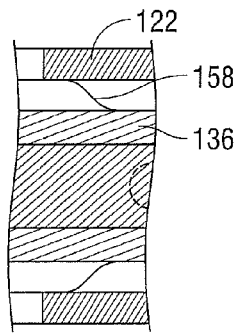
FIG. 5B is a partial, schematic view of an alternate embodiment of a distal end seal in accordance with the present disclosure.

FIG. 5B depicts an alternate embodiment of a seal for preventing contaminants from entering the outer shaft member 122. A wiper seal 158 is provided between the outer shaft member 122 and the knife 136. The wiper seal 158 may be constructed of a generally flat flap of an elastomeric or flexible material circumscribing and fixedly coupled to an interior of the outer shaft member 122. The wiper seal 158 may flex to maintain contact with the knife 136 as the knife 136 moves in a longitudinal direction. Additional wiper seals (not shown) or other seals may be provided between the knife 136 and the drive rod 126 or between the outer shaft member 122 and the drive rod 126.

Figure 6:
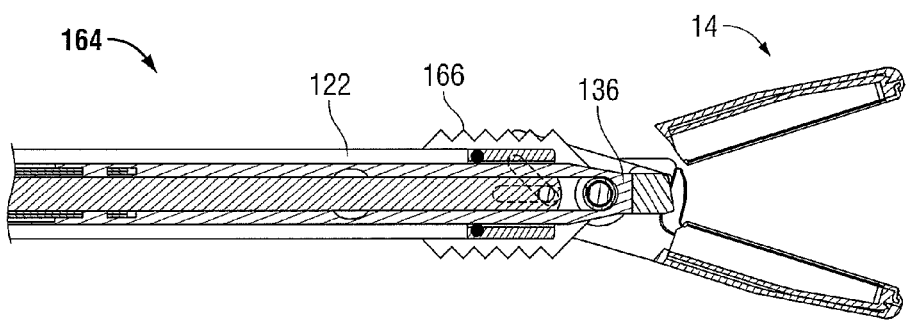
FIG. 6 is a partial, schematic view of an instrument including a contained actuation system with an alternate embodiment of a distal end seal in accordance with the present disclosure.

Referring now to FIG. 6, an alternate embodiment of a surgical instrument 164 includes an alternate seal for preventing contaminants from entering the outer shaft member 122. The instrument 164 includes a bellows seal 166 disposed between the outer shaft member 122 and the knife 136. The bellows seal includes folds that permit the bellows seal to expand and contract longitudinally to accommodate the motion of the knife 136 with respect to the outer shaft member 122. In some embodiments (not shown), a bellows seal may be provided between the end effector 14 and outer shaft member 122, or in other locations to discourage ingress of contaminants into the outer shaft member 122.

Figure 7:
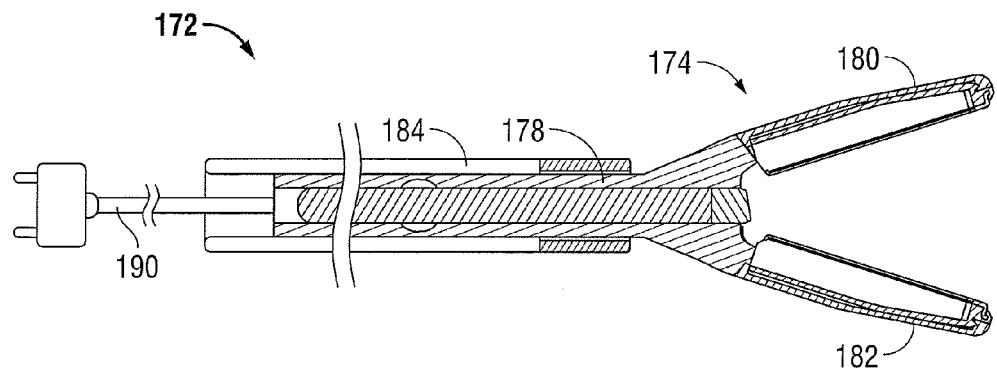
FIG. 7 is a schematic view of an alternate embodiment of a contained actuation system in accordance with the present disclosure.

Referring now to FIG. 7, an alternate embodiment of a surgical instrument 172 includes an alternate end effector 174 for facilitating cleaning and refurbishment of the instrument 172. The end effector 174 includes a drive tube 178 with a pair of jaw members 180, 182 formed at a distal end thereof. The drive tube 178 and jaw members 180, 182 are longitudinally movable with respect to an outer shaft 184. The jaws 180, 182 may be integrally formed with the drive tube 178 and may include flexible proximal ends that allow the jaws 180, 182 to close when retracted into the outer shaft 184. This type of mechanism for closing the jaw members 180, 182 reduces the number and complexity of components in the end effector 174, and may thus promote cleanliness and facilitate assembly of the instrument 172. In other embodiments (not shown), a pair of retractable jaw members may be coupled to one another by a pivot pin, and a compression spring (not shown) may be provided to bias the jaw members to a distal and open configuration.

A cable 190 is coupled to the end effector 174 and drive rod 178 such that the entire electrical system of the instrument 172 may be contained in a single module. Thus, no electrical connections must be established to assemble the instrument 172.

Figure 8:
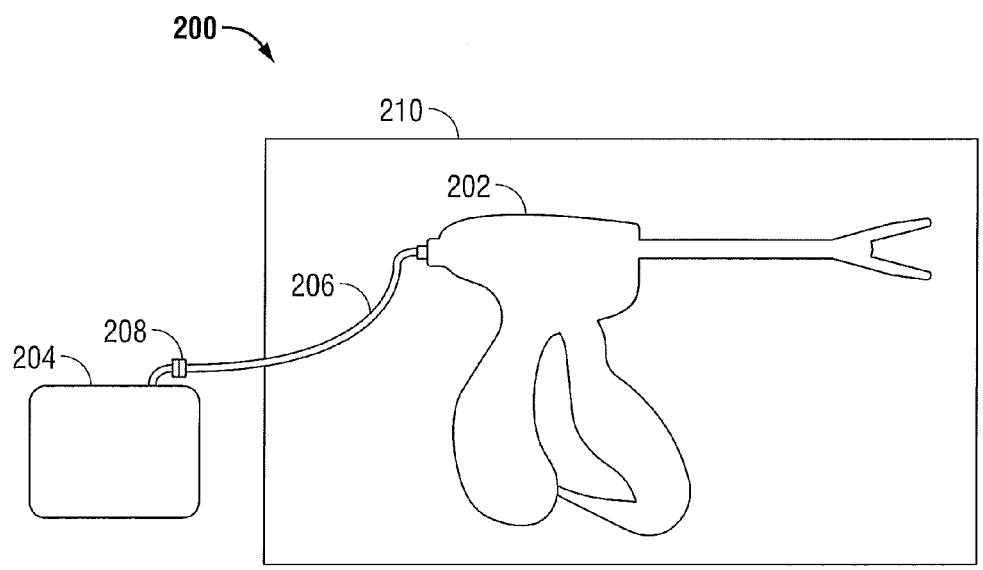
FIG. 8 is a schematic view of an alternate embodiment of an instrument in a sterile filed coupled to an actuation system positioned outside of the sterile field.

Referring now to FIG. 8, an alternate embodiment of an instrument 200 includes an instrument body 202 and a service module 204. The service module 204 may include components to provide electrical and mechanical power to the instrument body 202. For example, the service module 204 may include an electrosurgical generator and/or pneumatics or hydraulics configured to move parts of the instrument body 202. The instrument body 202 is mechanically and electrically coupled to the service module 204 by a conduit 206 including a separable connector 208. The connector 208 is disposed on the conduit 206 at a sufficient distance from the instrument body 202 to be located outside a surgical field 210 when the instrument 200 is in use.

Although the foregoing disclosure has been described in some detail by way of illustration and example, for purposes of clarity or understanding, it will be obvious that certain changes and modifications may be practiced within the scope of the appended claims.

What is claimed is:
1. A surgical instrument, comprising:
 a handle module including:
  at least one handle providing gripping surfaces for holding the instrument by hand;
  a post disposed within the handle module; and
  a slot defined by the handle module; and
 a drive assembly selectively removable from the handle assembly, the drive assembly including:
  an elongated shaft member defining a longitudinal axis;
  an end effector supported at a distal end of the elongated shaft member, the end effector including a pair of opposed jaw members wherein at least one of the jaw members is movable relative to the elongated shaft member between open and closed positions with respect to the other jaw member;
  a reciprocating drive member extending at least partially though the elongated shaft member, the drive member operably coupled to the end effector to induce movement of the jaw members between the open and closed positions in response to longitudinal reciprocation of the drive member;
  a motor operable to move the reciprocating drive member longitudinally through the elongated shaft;
  a housing substantially surrounding the motor and the reciprocating drive member, the housing substantially impervious to moisture;
  an actuator supported on the housing, the actuator operable to activate the motor;
  a post disposed within the housing; and
  a slot defined by the housing, wherein the post disposed within the handle module is configured to slide within the slot defined by the housing and wherein the post disposed within the housing is configured to slide within the slot defined by the handle module.

2. The surgical instrument according to claim 1, wherein the motor comprises a servomotor.

3. The surgical instrument according to claim 1, wherein the motor comprises a linear motor including an electrical coil supported on the elongated shaft member and a magnet supported on the reciprocating drive member, the magnet longitudinally movable in response to a current in the electrical coil.

4. The surgical instrument according to claim 1, wherein the drive assembly further includes a cable extending from the housing, the cable connectable to a source of electro surgical energy.

5. The surgical instrument according to claim 4, wherein the cable is in electrical communication with an electrical conduit extending through the elongated shaft member to transmit an electrosurgical current to the end effector.

6. The surgical instrument according to claim 1, wherein the post disposed within the housing is configured to snap-fit to the slot defined by the handle assembly.

* * * * *